United States Patent
Walling

(10) Patent No.: US 6,828,336 B2
(45) Date of Patent: Dec. 7, 2004

(54) NICOTINE-CONTAINING, CONTROLLED RELEASE COMPOSITION AND METHOD

(75) Inventor: John A. Walling, Union Grove, WI (US)

(73) Assignee: Cambrex Charles City, Inc., Charles City, IA (US)

( * ) Notice: Subject to any disclaimer, the term of this patent is extended or adjusted under 35 U.S.C. 154(b) by 0 days.

(21) Appl. No.: 10/429,420

(22) Filed: May 5, 2003

(65) Prior Publication Data

US 2003/0224048 A1 Dec. 4, 2003

Related U.S. Application Data

(63) Continuation-in-part of application No. 10/166,236, filed on May 28, 2002, now Pat. No. 6,586,449.

(51) Int. Cl.[7] ................. A61K 31/465; C07D 401/04
(52) U.S. Cl. ................. 514/343; 546/279.4; 514/343
(58) Field of Search .................. 546/279.4; 514/343

(56) References Cited

U.S. PATENT DOCUMENTS 3,845,217 A * 10/1974 Ferno et al. .................. 426/3
3,901,248 A * 8/1975 Lichtneckert et al. ....... 131/359
4,692,462 A  9/1987 Banerjee

* cited by examiner

Primary Examiner—Ceila Chang
Assistant Examiner—Janet L. Coppins
(74) Attorney, Agent, or Firm—Richard J. Hammond

(57) ABSTRACT

A nicotine product having a nicotine release rate of not less than 70% over a 10 minute period as well as a process to produce such product. Such product is produced by a process comprising the steps of
(a) preparing an aqueous solution of an organic polyol;
(b) mixing said aqueous solution of the organic polyol with a cation exchange resin selected from the group consisting of (i)—a methacrylic, weakly acidic type of resin containing carboxylic functional groups (ii)—polystyrene, strongly acidic type of resin containing sulfonic functional groups and (iii)—polystyrene, intermediate acidic type of resin containing phosphonic functional groups thereby forming a cation exchange resin mixture having some of its ion exchange sites partially blocked with said polyol;
(c) admixing with said mixture of step (b) an aqueous solution of nicotine to form a nicotine-coated cation exchange resin admixture; and
(d) removing water from said admixture.
The nicotine composition having a nicotine release rate of not less than 70% over a 10 minute period results.

14 Claims, No Drawings

NICOTINE-CONTAINING, CONTROLLED RELEASE COMPOSITION AND METHOD

This application is a Continuation-In-Part of U.S. application Ser. No. 10/166,236, filed May 28, 2002 now U.S Pat. No. 6,586,449 incorporated herein by reference.

FIELD OF INVENTION

This invention relates to a method for producing a nicotine-containing composition having a controlled release rate of nicotine. More particularly, this invention relates to a process for producing product comprising nicotine and a cation exchange resin, such product having a nicotine release rate of at least 70% over a 10 minute period.

BACKGROUND OF THE INVENTION

Nicotine is a well know, highly characterized alkaloid that can be isolated from the dried leaves of *Nicotiana tabacum*. Its numerous commercial uses include utilities such as a fumigant, an insecticide and the like. It is therapeutically valuable in the treatment of the smoking withdrawal syndrome. This treatment is based on the fact that the administration of nicotine into the body has been readily accomplished by the method of smoking, e.g., from cigarettes, pipes or cigars. The smoker experiences a satisfactory sensation from such administration. However, smoking may be associated with health hazards not necessarily associated with nicotine administration itself.

As a result, non-smoking methods have been devised to administer nicotine to the body. These include nicotine-containing chewing gums, nicotine-impregnated dermal patches, nicotine inhalers and the like. A variety of patents have disclosed such products.

In U.S. Pat. No. 4,692,462 discloses a transdermal drug delivery system having a drug reservoir composed, in part, of an ion exchange resin. The drug reservoir also contains water and a hydrophilic polymer gel. The presence of the water causes the drug to become unbound and therefore has a disadvantageously short shelf life.

WO 94/08572 is similar to the above-identified '462 patent but has a nonaqueous component, which increases the shelf life.

U.S Pat. No. 3,901,248 discloses a chewable smoking substitute composition that comprises a chewing gum base and nicotine in combination with certain saliva-insoluble cation exchange resins. When such composition is chewed, nicotine is released in small and reduced amounts into the mouth, within the first few minutes of chewing. The composition is marginally effective in inducing the pleasurable sensation of smoking that is typically desired from those engaged in the therapy that incorporates such chewing gum.

SUMMARY OF THE INVENTION

The present invention relates to a nicotine product having a nicotine release rate of not less than 70% over a 10 minute period as well as a process to produce such product Such a product is produced by a process comprising the steps of:
(a) preparing an aqueous solution of an organic polyol;
(b) mixing said aqueous solution of the organic polyol with a cation exchange resin selected from the group consisting of (i)—a methacrylic, weakly acidic type of resin containing carboxylic functional groups (ii)—polystyrene, strongly acidic type of resin containing sulfonic functional groups and (iii)—polystyrene, intermediate acidic type of resin containing phosphonic functional groups thereby forming a cation exchange resin mixture having some of its ion exchange sites partially blocked with said polyol;
(c) admixing with said mixture of step (b) an aqueous solution of nicotine to form a nicotine-coated cation exchange resin admixture; and
(d) removing water from said admixture.
The nicotine composition having a nicotine release rate of not less than 70% over a ten minute period results.

DESCRIPTION OF THE PREFERRED EMBODIMENTS

In accordance with the present invention, a process, product from such process and composition resulting from this process are disclosed. The composition is one that contains nicotine. The nicotine in the composition herein, has a release rate of not less than 70% over a period of 10 minutes. The method by which such release rate is determined is described in more detail in the U.S.P. Official Monograph, Volume 25, pages 1225 and 1226, incorporated herein by reference.

The product produced by the process according to the present invention contains, in addition to the above-disclosed nicotine, a cation exchange resin and an organic polyol.

Any nonionic pharmaceutical grade cationic ion-exchange resin used to bind anionic molecules at the ion exchange sites may be employed in this invention. Examples of such cationic materials are: the those bearing a carboxylic acid group, such as a weakly acidic type of resin containing carboxylic functional groups (these resins are typically derived from polymers or copolymers of methacrylic acid or polymethacrylic acid); the strongly acidic type of resins containing sulfonic functional groups (these resins are typically derived from polymers or copolymers of styrene or copolymers of styrene and divinylbenzene); or the intermediate acidic type of resins containing phosphonic acid functional groups (these resins are typically derived from polymers of styrene or copolymers of styrene and divinylbenzene).

Cationic ion exchange resins are well know in the art and the present invention encompasses all of these. Representative cation exchange resins of use in accordance with the present invention are disclosed in U.S. Pat. No. 3,901,258 incorporated herein by reference. The preferred cation exchange resins are those known in the art as the Amberlite® resins and include, for example, Amberlite® IR-20, Amberlite® IRP-69, Amberlite® IRP-64, Amberlite® IRP-58, Amberlite® IRC-50, Amberlite® IRP-69, etc.

The product in accordance with the present invention also contains as organic polyol. The organic polyol is a non-toxic $C_2$ to $C_{12}$ linear or branched hydrocarbon having at least 2 hydroxy groups or a non-toxic $C_5$ to $C_{12}$ cyclic or heterocyclic hydrocarbon having at least 2 hydroxy groups. The former compounds are illustrated by the polyhydric alcohols such as 1,3-dihydroxypropane, hexylene glycol, glycerin, sorbitol etc., the latter by inositol and the carbohydrates such as glucose, sucrose, etc.

In carrying the process in accordance with the present invention, it is necessary to combine the organic polyol with the cation exchange resin to form a mixture (slurry). Any form of mixing is acceptable. However, it is important that the ratio of cation exchange resin to organic polyol is from about 1:1 to about 5:1, i.e., from about 1 gram of resin per gram of polyol to about 1 gram of resin per 200 mg. of polyol. Preferably, the ratio of cation exchange resin to organic polyol is from about 2:1 (1 gram of resin per 500 mg of polyol) to about 4:1 (1 gram of resin per 250 mg. of polyol), most preferably about 2.5:1 (1 gram of resin per 400 mg. of polyol).

To the mixture (slurry) formed as disclosed above, is admixed an aqueous solution of nicotine. The concentration of nicotine in the aqueous solution of nicotine is from about 5% by weight to about 40% by weight, i.e., about 50 mg to about 400 mg of nicotine in each gram of solution. Preferably there is about 10% to about 30% by weight, i.e., about 100 mg to about 300 mg, of nicotine for each gram of solution. Most preferably, the amount of nicotine for each gram of solution is about 150 mg, i.e., about 15% by weight.

The ratio of cation exchange resin to nicotine is from about 2:1 to about 10:1, i.e., 1 gram of resin per 500 mg of nicotine to about 1 gram of resin per 100 mg of nicotine.. Preferably, the ratio of cation exchange resin to nicotine is from about 3:1 to about 6:1, i.e., 1 gram of resin per 333 mg of nicotine to about 1 gram of resin per 167 mg of nicotine. Most preferably, the rato of cation exchange resin to nicotine is about 4:1, i.e., 1 gram of resin per 250 mg of nicotine.

The admixture, which is a water slurry of the cation exchange resin incorporating nicotine and the organic polyol is then dried to remove the water. Such drying can be carried out by any conventional means, i.e., dried over a purge of nitrogen, dried under vacuum, etc.. However, it should be noted that drying the admixture at temperatures in excess of 75–80° C. cause the disadvantageous loss of nicotine and should be avoided.

The dried admixture, which is an lightly colored, brown powder, is typically sieved to a substantially uniform particle size before being used.

The composition of the final powdered product, i.e., the polyol modified-nicotine containing cation exchange resin of the present invention comprises 10 to 499 mg of nicotine, 10 to 499 mg of polyol and 980 to 2 mg of resin. Preferably, the composition of the final product is 100 to 200 mg of nicotine, 200 to 300 mg of polyol 600 to 500 mg of ion exchange resin. In its most preferred composition it has the following concentration of components: 150 mg nicotine; 240 mg of polyol; and 610 mg of ion exchange resin.

The following Examples demonstrate the process pf the present invention and the compositions resulting from such process. These Examples should not be regarded as limiting the invention in any sense.

EXAMPLES

Nicotine/Resin Process

A 1 liter 3-neck, jacketed round bottom flask fitted with external heating/cooling, mechanical agitation and a nitrogen gas inlet is charged with Amberlite® IRP-64 resin (61.0 grams) and a solution of the polyol (24.0 grams) and water (146.4 grams). The mixture is agitated for at least 2 hours at 20–25° C. under a nitrogen atmosphere. A solution of nicotine (15.0 grams) and water (36.6 grams) is then added to the mixture and agitation is continued for 1 additional hour.

On completion of the above procedure, the flask is reconfigured for vacuum distillation. Water is distilled from the reaction mixture at a temperature not to exceed 70° C. and at $\geq 25''$ of vacuum. The process is halted when water stops being collected as distillate. At that point, the reaction mixture (the residue remaining in the flask) is a solidified mass. This solid material is transferred to a drying dish and further dried in a vacuum at 50–60° C. with nitrogen purge. The mixture is considered dry when a Karl Fisher analysis shows the water content in the solid mass to be <5%. The final dry product is a brown powder.

A number of polyols illustrative of the present invention were individually processed in the above Nicotine/Resin Process. The dried mixtures containing these different polyols were analyzed to determine nicotine concentration and release rate of nicotine according to the procedure set forth in the U.S.P. Official Monograph, Volume 25, pages 1225 and 1226. The results for the illustrative polyols are reported below in the Table 1.

TABLE 1

| Example | Composition | Nicotine Assay mg | Nicotine Assay % | Nicotine Released mg | Nicotine Released % |
|---|---|---|---|---|---|
| 1 | Nicotine and glycerol | 41.1 | 15.31 | 4.5 | 71 |
| 2 | Nicotine and sorbitol | 39.3 | 15.61 | 4.4 | 72 |
| 3 | Nicotine and 1,6-hexanediol | 39.9 | 14.93 | 4.4 | 74 |
| 4 | Nicotine and 1,2-propanediol | 39.4 | 15.62 | 4.4 | 72 |
| 5 | Nicotine and inositol | 40.7 | 14.40 | 4.5 | 76 |
| 6 | Nicotine and sucrose | 40.1 | 15.63 | 4.8 | 77 |
| Comparative | Nicotine and no polyol | 40.0 | 15.44 | 4.0 | 65 |

While the above results of the above Examples appear unequivocal, i.e., the polyols enhance the release rate of nicotine from the nicotine/resin mixture, in order to establish the precision of this U.S.P. method, a precision study was carried out. It is shown below in Tables 2A and 2B.

TABLE 2A

NO POLYOL

| Example | Assay % | Sample mg | Nicotine Released % | Nicotine Released mg |
|---|---|---|---|---|
| 1 | 15.47 | 39.50 | 65.87 | 4.02 |
| 2 | 15.53 | 38.70 | 65.92 | 3.96 |
| 3 | 15.45 | 41.00 | 65.10 | 4.12 |
| 4 | 15.42 | 41.80 | 62.35 | 4.02 |
| 5 | 15.45 | 39.30 | 63.82 | 3.88 |
| 6 | 15.31 | 39.90 | 66.14 | 4.04 |
| average | 15.44 | 40.03 | 64.87 | 4.01 |
| std dev | 0.07 | | 1.50 | |
| % rsd | 0.48 | | 2.31 | |

TABLE 2B

WITH SORBITOL

| Example | Assay % | Sample mg | Nicotine Released % | Nicotine Released mg |
|---|---|---|---|---|
| 1 | 15.48 | 38.00 | 73.45 | 4.32 |
| 2 | 15.21 | 39.30 | 69.27 | 4.14 |
| 3 | 16.04 | 42.00 | 70.75 | 4.77 |
| 4 | 15.76 | 38.20 | 71.83 | 4.32 |
| 5 | 15.45 | 39.80 | 71.50 | 4.40 |
| 6 | 15.73 | 38.70 | 72.85 | 4.43 |
| average | 15.61 | 939.33 | 71.61 | 4.40 |
| std dev | 0.29 | | 1.50 | |
| % rsd | 1.85 | | 2.09 | |

The data in Tables 2A and 2B show that the nicotine release rate for the sorbitol-containing sample of 72% is reproducible. Although one sample was measured at 69.3% it is within the normal fluctuation of the method (±2%). It should be noted that this apparent failure is remedied upon reassay, which is a normal procedure for samples that show a release rate of <70%.

The release rate for the No Polyol is also confirmed by this precision study. It always gives a value of <70%.

I claim:

1. A nicotine containing composition in powder form comprising about 10 to about 499 mg per gram of an organic polyol, about 2 to about 980 mg per grain of a cation exchange resin selected from the group consisting of (i)—a methacrylic, weakly acidic type of resin containing carboxylic functional groups (ii)—polystyrene, strongly acidic type of resin containing sulfonic functional groups and (iii)—polystyrene, intermediate acidic type of resin containing phosphoric functional groups, said cation exchange resin having some of its ion exchange sites partially blocked with said polyol and about 10 to about 499 mg per gram of nicotine produced by the process comprising the steps of (a) preparing an aqueous solution of the organic polyol (b) mixing said aqueous solution of the organic polyol with said cation exchange resin thereby forming a mixture of a cation exchange resin having some of its ion exchange sites partially blocked with said polyol (c) admixing with said mixture of step (b) an aqueous solution of nicotine to form a nicotine-coated cation exchange resin admixture and (d) removing water from said admixture to produce said nicotine-containing composition in powder form having a nicotine release rate of not less than 70% over a ten minute period.

2. A nicotine containing composition in powder form comprising about 10 to about 499 mg per gram of an organic polyol selected from a non-toxic $C_2$ to $C_{12}$ linear or branched hydrocarbon having at least 2 hydroxy groups, or a non-toxic $C_5$ to $C_{12}$ cyclic hydrocarbon having at least 2 hydroxy groups, which is selected from the group consisting of dihydroxypropane, glycerol, hexanediol, propanediol, and inositol, about 2 to about 980 mg per gram of a cation exchange resin
selected from the group consisting of(i)—a methacrylic, weakly acidic type of resin containing carboxylic functional groups (ii)—polystyrene, strongly acidic type of resin containing sulfonic functional groups and (iii)—polystyrene, intermediate acidic type of resin containing phosphoric functional groups said cation exchange resin having some of its ion exchange sites partially blocked by said organic polyol and about 10 to about 499 mg per gram of nicotine said nicotine-containing composition having a nicotine release rate of not less than 70% over a ten minute period.

3. The product according to claim 1 wherein the concentration of organic polyol in said aqueous solution of organic polyol is from about 5% by weight to about 60% by weight.

4. The product according to claim 1 wherein the concentration of nicotine in said aqueous solution of nicotine is from about 100 mg to about 300 mg for each gram of solution.

5. The product according to claim 1 wherein the ratio of cation exchange resin to nicotine is from about 2:1 to about 10:1.

6. The product according to claim 1 wherein the ratio of cation exchange resin to nicotine is from about 3:1 to about 6:1.

7. The product according to claim 1 wherein the ratio of cation exchange resin to nicotine is about 4:1.

8. The product according to claim 1 wherein the ratio of cation exchange resin to organic polyol is from about 1:1 to about 5:1.

9. The product according to claim 1 wherein the ratio of cation exchange resin to organic polyol is from about 2:1 to about 4:1.

10. The product according to claim 1 wherein the ratio of cation exchange resin to organic polyol is about 2.5:1.

11. The product according to claim 1 wherein said organic polyol is a $C_2$ to $C_{12}$ linear or branched hydrocarbon having at least 2 hydroxy groups or a $C_5$ to $C_{12}$ cyclic or heterocyclic hydrocarbon having at least 2 hydroxy groups.

12. The product according to claim 1 wherein said organic polyol is fructose, sucrose or glycerine.

13. The composition according to claim 2 wherein said organic polyol is a $C_2$ to $C_{12}$ linear or branched hydrocarbon having at least 2 hydroxy groups or a $C_5$ to $C_{12}$ cyclic hydrocarbon having at least 2 hydroxy groups.

14. The composition according to claim 2 wherein said organic polyol or glycerine.

* * * * *